United States Patent [19]

Voris et al.

[11] Patent Number: 4,471,657

[45] Date of Patent: Sep. 18, 1984

[54] DIGITAL ULTRASONIC STRESS MEASURING METHOD AND APPARATUS

[75] Inventors: Hugh A. Voris, Los Gatos; Kenneth R. Boyd; David A. Vossbrink, both of Santa Cruz, all of Calif.

[73] Assignee: Stresstel Corporation, Scotts Valley, Calif.

[21] Appl. No.: 262,796

[22] Filed: May 12, 1981

[51] Int. Cl.³ ............................................ G01N 29/00
[52] U.S. Cl. ...................................... 73/597; 73/761
[58] Field of Search ................ 73/597, 629, 761, 602, 73/598; 367/108

[56] References Cited

U.S. PATENT DOCUMENTS

| | | | |
|---|---|---|---|
| 3,759,090 | 9/1973 | McFaul et al. | 73/597 |
| 3,783,679 | 1/1974 | Jackson | 73/609 |
| 3,985,022 | 10/1976 | Brewster et al. | 73/67.8 R |
| 4,014,208 | 3/1977 | Moore et al. | 73/761 X |
| 4,114,455 | 9/1978 | Walker | 73/597 |
| 4,295,377 | 10/1981 | Couchman | 73/761 |
| 4,307,611 | 12/1981 | Opara | 73/597 |

OTHER PUBLICATIONS

"Ultrasonic Testing of Materials", by Krautkramer, pp. 280–281, published by Springer-Verlaz, New York, 1977.

Primary Examiner—James J. Gill
Attorney, Agent, or Firm—Limbach, Limbach & Sutton

[57] ABSTRACT

A digital ultrasonic extensometer for measuring the stress in a tensile load member, such as a bolt under load, the extensometer including a transducer permanently or temporarily in contact with the load member being measured, an intelligent processing means controlled time interval measuring means which generate a number of signals for energizing the transducer, the transducer, in turn, receiving the return pulse from the far end of the member under test and converting it into an electrical signal which is amplified and provided to the digital circuitry; the time interval measuring means then measure the number of clock pulses and portions of clock pulses during the period of time from the pulser signal to the receipt of the signal return from the end of the test member, provide a plurality of such pulse groups to the intelligent processing means, which enhance the accuracy of measurement by computational averaging computing, and indicate on a digital display and on an included paper printer, the computed indication of stress, length, elongation, temperature, and test member identifying information, such parameters being stored in the intelligent processing means having been either manually provided or internally determined as applicable.

16 Claims, 5 Drawing Figures

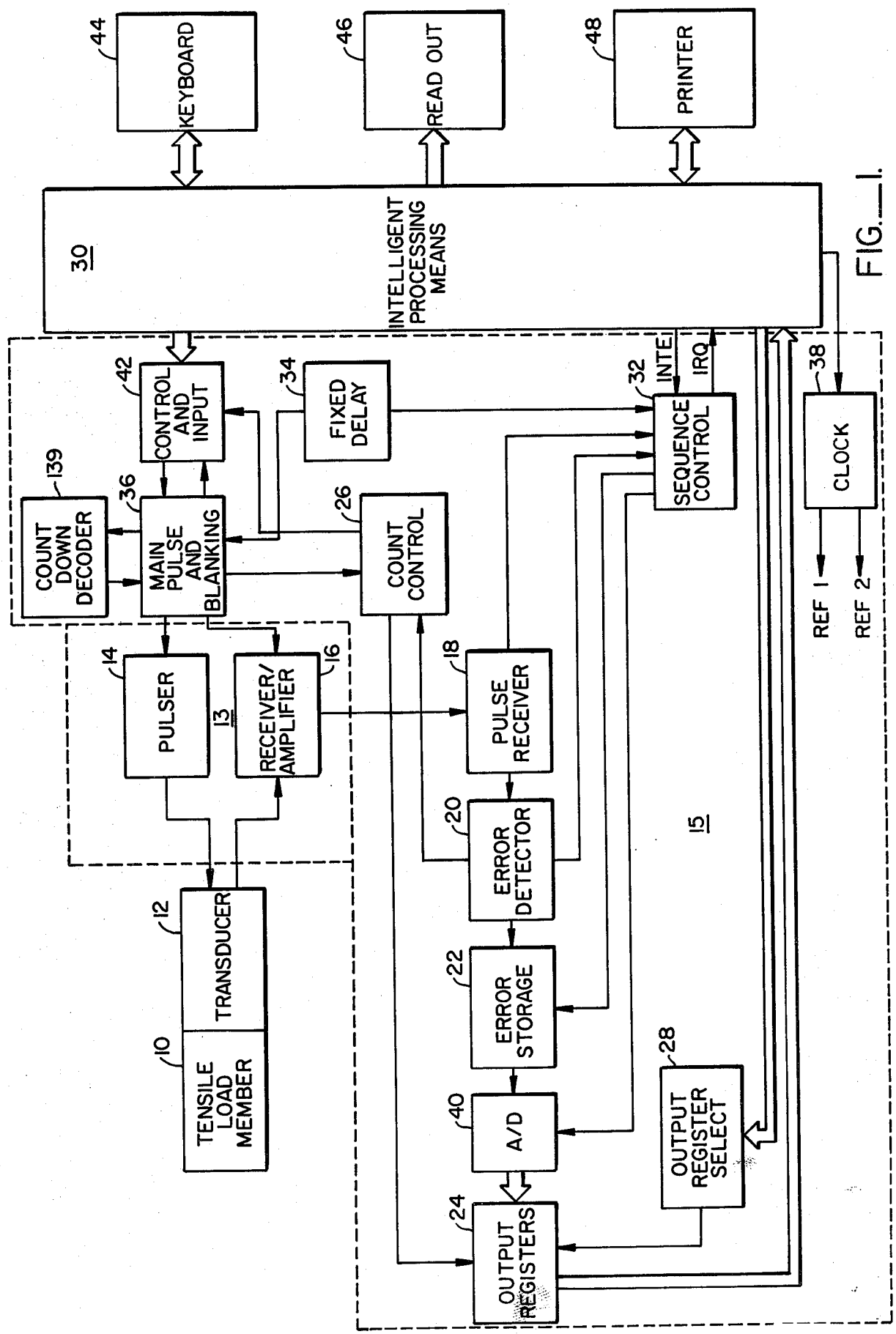
FIG._1.

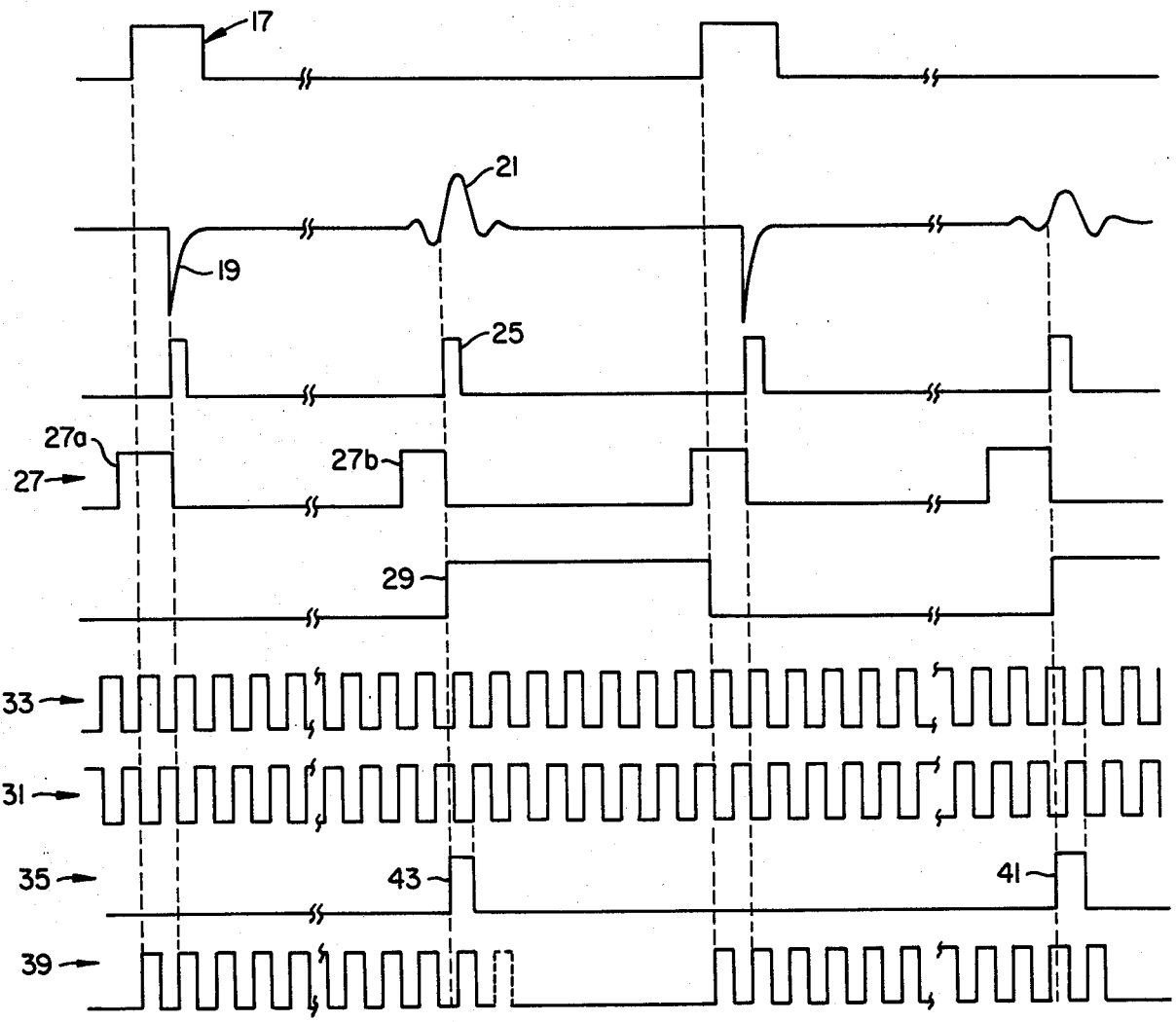
FIG._2.

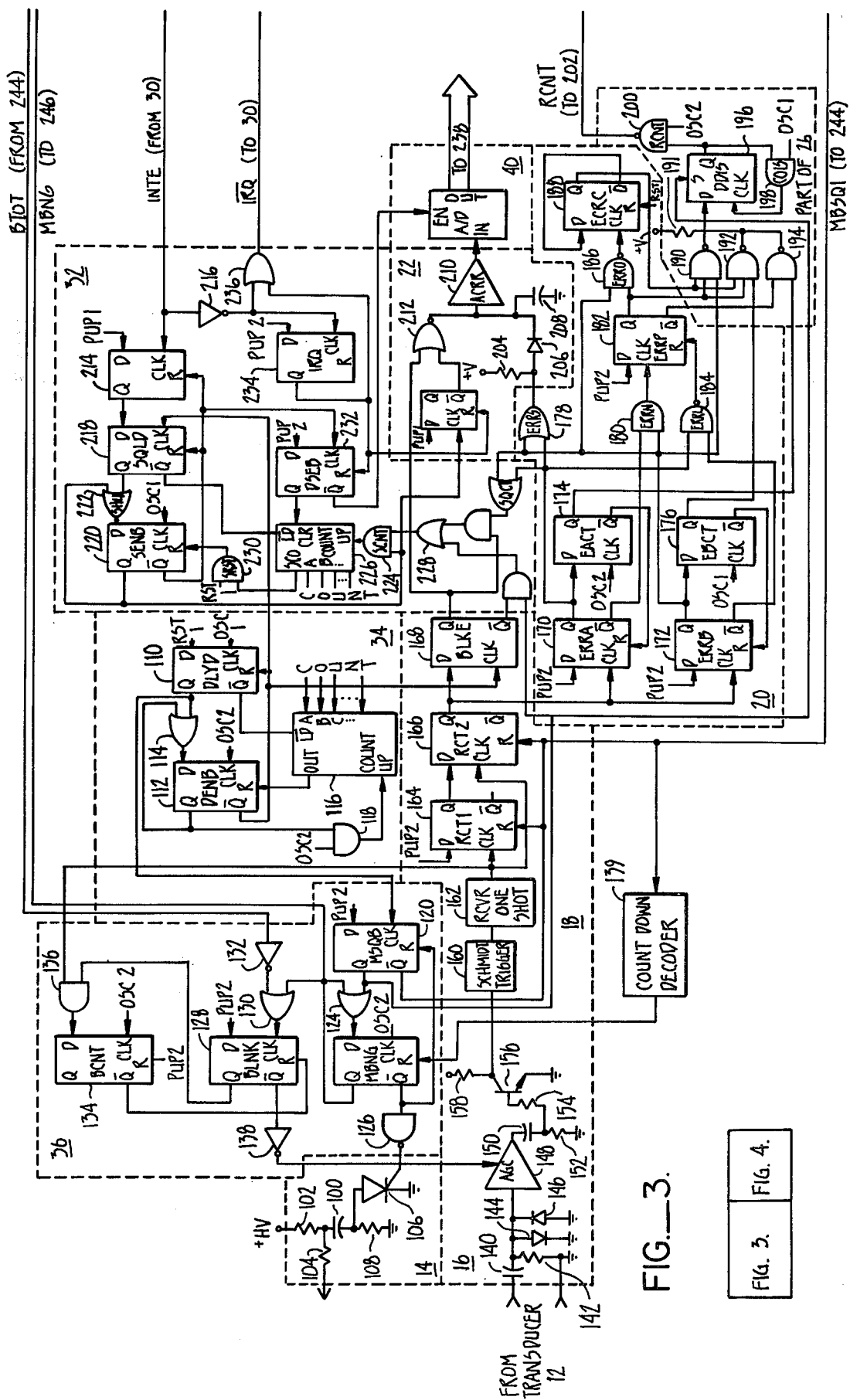
FIG._3.

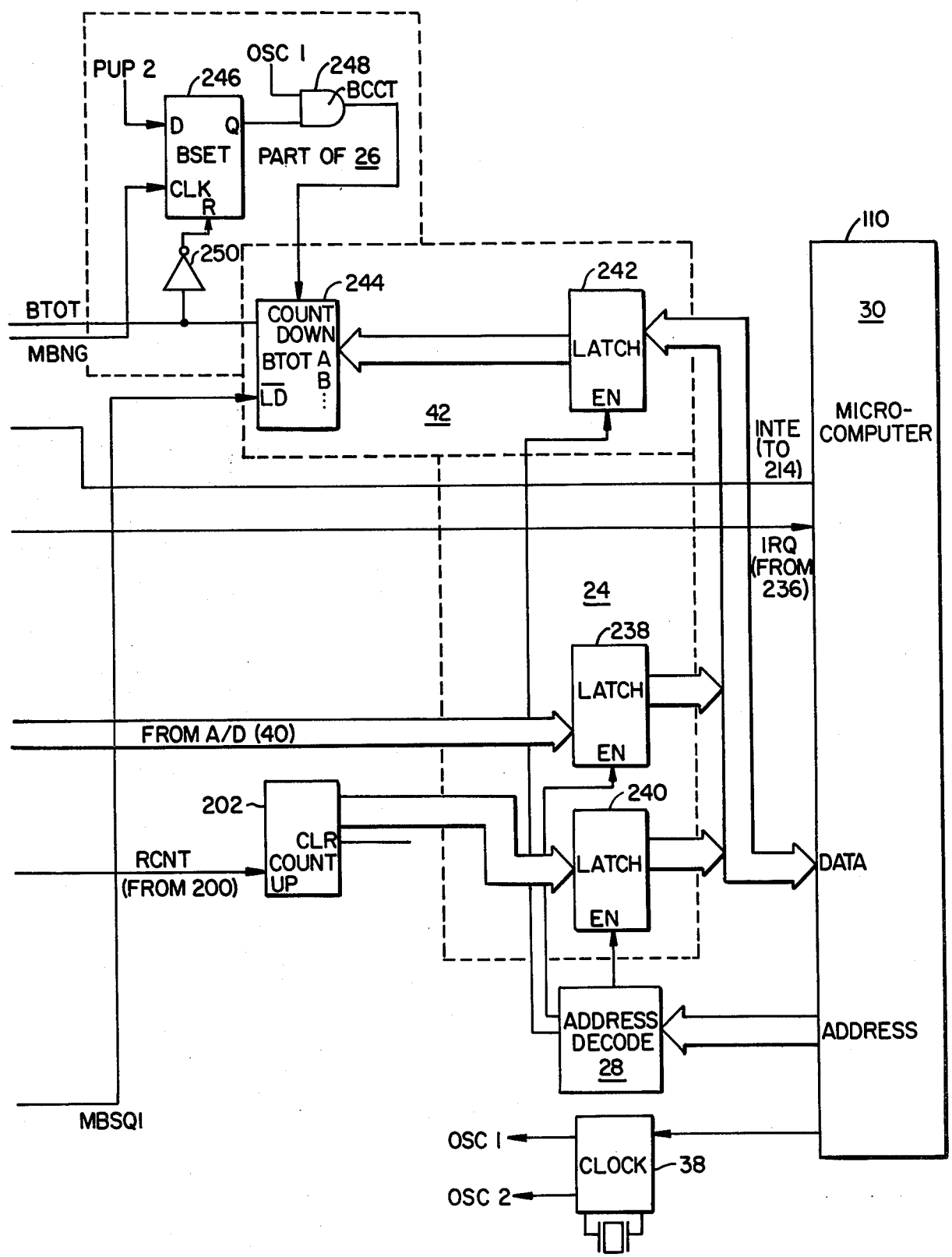
FIG._4.

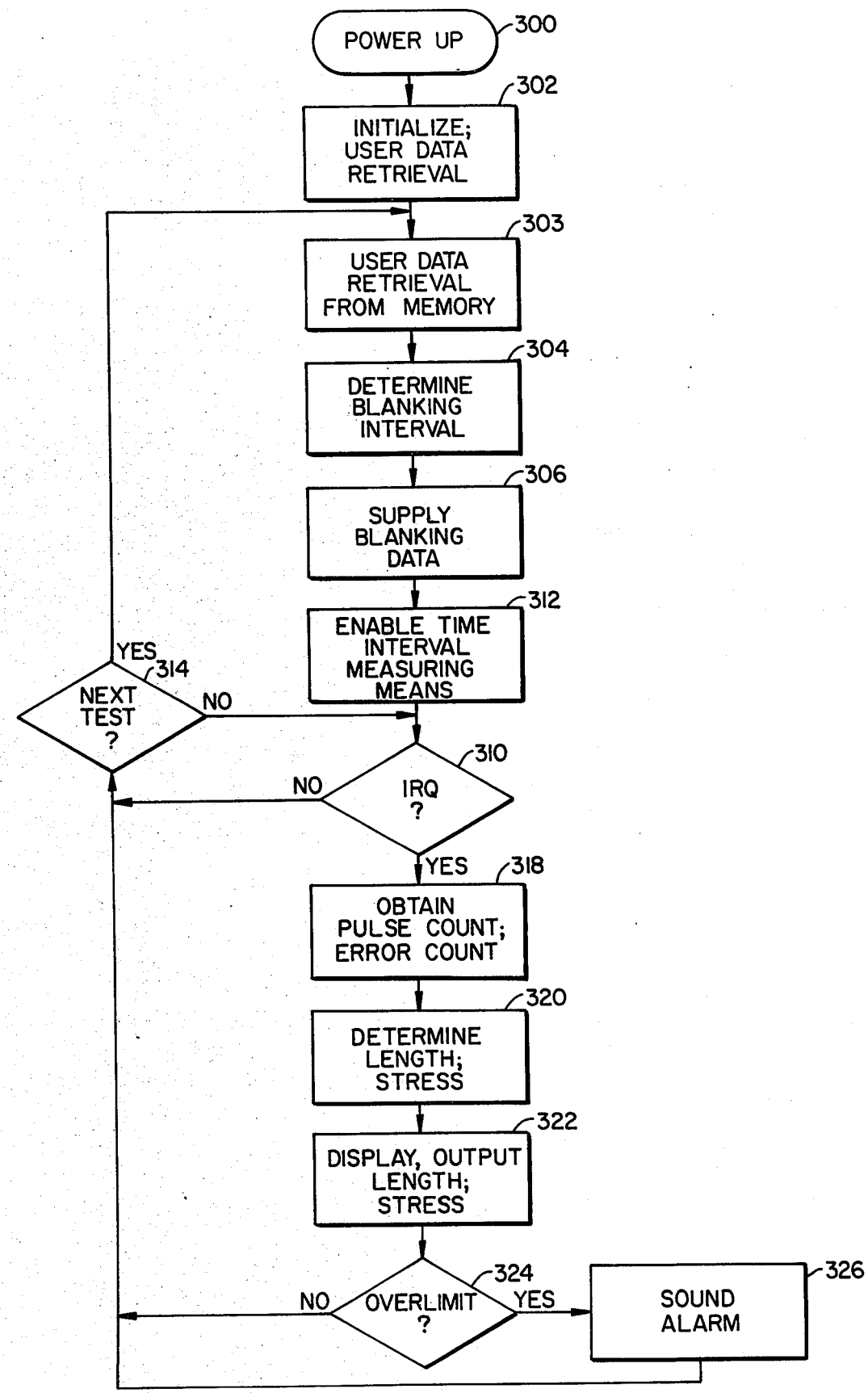
FIG._5.

DIGITAL ULTRASONIC STRESS MEASURING METHOD AND APPARATUS

BACKGROUND OF THE INVENTION

The invention described herein is in general an intelligent ultrasonic measuring apparatus. More specifically, in this invention is directed to a means of measuring the average tensile stress within a bolt or tensile load member when the fastener is tightened against the structure which it fastens.

The accurate measurement of tensile stress in threaded fasteners is essential to control of the clamping force exerted by such fasteners, and the prevention of failure of the fastener by determination of the tensile stress relative to the yield stress of the fastener material.

Throughout the history of threaded fasteners, a number of devices have been developed and employed with the purpose of measuring and/or controlling such tensile stress.

Torque wrenches attempt to control such stress by determining the rotational energy applied to the nut, such measurement is highly inaccurate due to the variable friction forces between nut and bolt and nut and structure or washer.

Hydraulic tensioners apply accurate tensile load to the fastener. However, relaxation of this load upon the nut make accurate control extremely difficult.

Mechanical micrometers have been employed to measure the elongation of a fastener upon tightening which occurs in proportion to the applied tensile stress. Such devices are extremely time-consuming to operate and subject to operator error.

Various ultrasonic (Echo ranging) extensometers ranging from standard thickness gauges which measure subsequent lengths of the fastener to units which measure elongation directly are generally limited in the overall length of the fastener or the elongation which can be measured. These units measure the apparent change in length of the fastener thereby making no adjustment for the differing sonic phenomena occurring in the stressed and unstressed portion of the fastener, nor are these units readily adaptable to various fastener materials or change in fastener temperature. Thus, accurate correlation of apparent change in fastener length indicated by these units is not practical.

It is, therefore, apparent that the devices described above do not provide a practical means of measuring or controlling compressive or tensile stress in bolts or similar structural members. It is for this specific purpose that we have developed our invention.

Typical of these ultrasonic extensmeters is McFaul, et al., U.S. Pat. No. 3,759,090 in which an analog device for measuring the elongation of a bolt is disclosed. In McFaul, an ultrasonic pulse was inserted into the bolt to be measured, and the echo pulse was received and processed. The instant of receipt of the echo pulse for a non-elongated bolt was adjusted to occur just subsequent to a periodically occurring marker pulse, the time period between each marker pulse occurrence corresponding to an indicatable elongation of the bolt. The time period between the incidence of the echo pulse and the occurrence of the next marker pulse was converted into an analog meter reading, the analog meter needle deflection being calibrated to indicate units of elongation. As the bolt was elongated, the time for the applied pulse to travel down the length of the bolt and to be reflected back being increased. This resulted in the time period between the incidence of the echo pulse and the occurrence of the next reference pulse being shortened. As a result, the meter indication also decreased. In this manner, as the bolt was elongated, the user could monitor the change in elongation by watching the meter reading decrease.

While the ultrasonic extensometer of McFaul permitted the user to monitor an indication of elongation, the actual stress to which the bolt was being subjected was unknown. Additionally, because the meter indicated the time period between each receipt of the echo pulse and the next occurring reference pulse, the movement of the meter was susceptible to the usual jitter which results when a series of individual samples are each displayed. Additionally, because of variations in echo pulse amplitude from sample to sample, the exact time of receipt of the echo pulse was not constant from sample to sample. This further added to the jitter in the meter display, as well as to a degradation in the accuracy of the indicated elongations. Because the ultrasonic extensometer of McFaul require that the user initially "zero-out" the non-elongated portion of the bolt by setting the received echo pulse to occur just subsequent to the reference pulse, the elongation reading which resulted was further compromised by any "zeroing" error which occurred. Additionally, the analog circuits used to process the ultrasonic signals were susceptible to both short term and long term drift causing excessively long warm-up times and unreliable repeatability of readings.

SUMMARY OF THE INVENTION

The foregoing and other problems of prior art stress measuring apparatuses and methods are overcome by the present invention of a method and apparatus for measuring the length and stress in a tensile load member, the load member having a first and a second end, the method and apparatus being of the type in which a transducer is energized to insert an ultrasonic pulse into the first end of the load member, the transducer receiving the pulse echo which is reflected back from the second end of the load member, the transducer converting the echo into an equivalent electrical signal. The apparatus comprises time interval measuring means for determining the elapsed time between the transducer energization and the receipt of the pulse echo, for a loaded and unloaded tensile load member; and intelligent processing and control means which receive the elapsed time data from the time interval measuring means, and user-supplied information, for controlling the time interval measuring means and for deriving a plurality of parameters describing the tensile load member, including length and stress, from the elapsed time data and user-supplied information.

The apparatus implements a method for measuring a time interval between the initiation of an energizing signal and the receipt of the return signal, comprising the steps of counting the numbers of cycles of a first clock which occur between the initiation of the energizing signal and the receipt of the return signal, the first clock being synchronized to the initiation of the energizing signal and having a predetermined frequency; generating a second clock having the same frequency as the first clock and having a predetermined phase difference from the first clock; measuring a first clock interval between the receipt of the return signal and a subsequent specified state in the first clock signal, and measuring a second clock interval between receipt of the return signal and the occurrence of the specified state in the second clock signal; detecting the longer of the first clock interval and the second clock interval; compensating the selected clock interval for the phase difference between the first clock and the second clock; combining the cycle count with the selected clock interval, and converting the cycle count and compensated selected clock interval into units of time. The above method reduces quantization error problems which arise when the incremental periods being used to measure an interval is large with respect to the accuracy which is being sought.

In the method of the present invention, the time interval measurements which are transferred to the intelligent processing and control means are gathered over a substantial number of measurement cycles, or samples, thereby providing a more accurate time interval value. The time interval measuring procedure requires that the point in time which is deemed to represent the receipt of the echo pulse is designated as the first or second zero-crossing of the received analog pulse echo signal. It has been discovered that while the amplitude and duration of an echo pulse can vary from sample to sample, the first and second zero-crossing of the received pulse echo signal are consistent from sample to sample.

The intelligent processing and control means control the windows through which the time interval measuring means receive the pulse echo from the tensile load member. These windows are automatically adjusted according to the material, the length of the tensile load member being measured, the amount of elongation to which the load member is being subjected, and other parameters. The intelligent processing and control means accept the time interval data from the time interval measuring means and derive therefrom an indication of the amount of stress to which the tensile load member is being subjected. This determination, while based upon the measured time interval from the time interval measuring means, also considers a variety of other factors, including temperature, tensile load member material, velocity change due to stress forces on the tensile load member materials, overall length, elasticity of the tensile load member material, as well as thermal expansion of the tensile load member material. The intelligent processing and control means provide actual average stress over the loaded length of the bolt and other data to the user by indicating means which include visual means and electronic signal means.

The apparatus and method of the present invention thereby provides actual stress data, as opposed to solely elongation data. As such, the user need not resort to tables or precalculated values or the interpolations which often accompany such sources, to determine whether or not the tensile load member is being properly loaded. The implementation of the zero-crossing reference point for the received echo signal, and the sample averaging within the time interval measuring unit greatly reduces the amount of jitter and uncertainty in measurement which was a problem in previous elongation measuring apparatuses. Control by the intelligent processing and control means of the time interval measuring means reduces the amount of operator adjustment necessary to obtain an accurate reading. The consideration of temperature, elasticity, thermal expansion, and other physical phenomena in the determination of the stress provides for a more realistic and accurate stress measurement.

It is, therefore, an object of the present invention to provide a method and apparatus for measuring the stress in a tensile load member.

It is a further object of the present invention to provide a method and apparatus for measuring the stress in a tensile load member, wherein the time interval measurement is accomplished using a two-phase clock so that quantization error is reduced.

It is a still further object of the present invention to provide a stress measuring method and apparatus wherein physical phenomena such as velocity variation in stress materials, elasticity, thermo-expansion, and velocity variations by material are considered in obtaining the stress value.

It is another object of the present invention to provide a method and apparatus for measuring stress in a tensile load member, wherein a time interval between the injection of an ultrasonic pulse and the reception of the pulse echo is measured digitally, and further wherein the point at which the echo pulse is received is determined by the first or second zero-crossing of the received echo pulse signal.

It is another object of the present invention to provide a method and apparatus for measuring the stress in a tensile load member wherein an intelligent processing and control means regulates the timing and sampling rate of a time interval measuring means.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWING

FIG. 1 is an overall block diagram of the apparatus of the present invention.

FIG. 2 illustrates the timing and waveform shapes at significant points within the apparatus of the present invention.

FIG. 3 is a simplified schematic diagram of a part of the apparatus of the preferred embodiment of the present invention.

FIG. 4 is a simplified schematic diagram of a part of the apparatus of the preferred embodiment of the present invention.

FIG. 5 is a flow diagram which illustrates the method by which stress information is obtained through the interaction of the time interval measuring means and the intelligent processing and control means of the present invention.

DETAILED DESCRIPTION OF THE PREFERRED EMBODIMENT

Referring more particularly to FIG. 1, the general operation of the present invention will now be described.

Conceptually, the apparatus of the present invention can be divided into several functional elements or blocks.

A pulser-receiver 13 produces a sharp, high voltage spike (or pulse) which is transmitted to a piezo electric crystal transducer 12, which is physically held in contact through a coupling medium to the end of the threaded fastener or tensile load member 10. The electrical pulse is converted by the crystal to a high frequency ultrasonic pulse which is transmitted along the length of the load member 10. A portion of this pulse is reflected by the opposite end of the load member 10 and returns to the transducer 12, where it is converted again to an electrical echo pulse and is transmitted to the pulse receiver 13. The receiver portion of the pulser-receiver 13 detects the arrival of the echo pulse by identifying the point at which the energy of the signal passes from negative to positive voltage (zero crossing detection). This unique feature provides precise detection of the pulse return independent of the pulse magnitude. Further, the receiver is controlled by instructions produced by an intelligent processing means 30 so that only the first echo from the end of the fastener (or other preselected point) is detected, and all other erroneous or resonant echos are ignored.

Time interval measuring means 15 are controlled by the intelligent processing and control means 30. The measuring means 15 are activated by the outgoing pulse of the pulser-receiver 13, and upon detection of the echo pulse by the receiver-portion, measures the elapsed time with respect to the number of clock pulses and portions of a clock pulse produced by a reference oscillator 38. Further, the measuring means are instructed by the intelligent processing and control means 30 as to the number of such pulse-echo intervals to be accumulated during a sampling period, thus providing dynamic averaging of the resulting data.

The intelligent processing and control means 30 provide numerous functions in coordinating the interaction of the pulser-receiver 13 and the time interval measuring means 15, as described above. The intelligent processing and control means 30 monitors the collection of pulse data and processes those data to produce an accurate conversion to the change in fastener length or the stress applied to the tensile load member 10. The intelligent processing and control means 30 are provided with physical constants for a substantial number of tensile load member materials or specific load members. These constants and the applicable equations permit interpretation of the pulse data with respect to the variation of sonic velocity within various materials, elasticity of various materials, thermal expansion of various materials, and the variation in these parameters with material temperature. Further, the intelligent processing and control means 30 provide for the variation of sonic velocity with respect to the level of applied stress, and the actual length of the tensile load member 10 to which stress is applied.

The functional operation of each of the above elements will now be described in greater detail. Please refer to FIGS. 1 and 2.

The tensile member 10 for which the stress measurement is sought to be obtained, is connected to a transducer 12. The transducer, in turn, is connected to a pulser 14 and a receiver/amplifier 16 which comprise the pulser-receiver 13 described above. The pulser 14, in response to an energization or energizing trigger signal 17, FIG. 2, outputs an energizing signal 19, FIG. 2, to the transducer 12. In response to this energizing signal or pulse, the transducer 12 inserts a high-energy, ultrasonic pulse into one end of the tensile load member 10. This ultrasonic pulse causes a shock wave to be transmitted down the length of the load member and to be reflected by the opposite end of the load member. This reflected pulse, or echo pulse, travels back along the length of the load member 10 to the end of the load member to which the transducer 12 is attached. When this echo signal reaches the transducer 12, the transducer converts this reflected wave into an equivalent electrical analog signal 21, FIG. 2. Previous to this, the transducer supplies the energizing pulse 19, FIG. 2, to the receiver/amplifier 16 where it is processed. The receiver/amplifier 16 detects the arrival of the echo pulse by identifying the first and second zero-crossing of the electrical pulse signal. When such a zero-crossing has been detected, the receiver/amplifier 16 outputs an echo received pulse 25, FIG. 2, having a predetermined duration.

Typically, the echo signal 21, FIG. 2, which is output by the transducer 12 is an alternating current signal having an amplitude, typically, of a few hundred millivolts and a duration of varying length. The energizing signal 19, FIG. 2, which is also received by the receiver/amplifier 16, typically, has an amplitude of a hundred volts or more of less than one microsecond duration. During normal operation of the pulser 14, the transducer 12, and the receiver/amplifier 16, a sequence of energizing signals are transmitted and the corresponding echo pulses received.

It is a common phenomenon that a shock wave travelling within the tensile load member can retain a significant amplitude even after being reflected back and forth within the tensile load member several times. As such, the transducer 12 will often receive echo pulses from the tensile load member which correspond to the third, fourth or fifth reflections. In order to distinguish between the desired energizing and first reflected echo pulse signals, and to discard the subsequent reflected signals, the receiver/amplifier 16 is provided with an AGC signal 27, FIG. 2, from blanking circuitry 36, to be described in detail later. This AGC signal 27 effectively shuts off the receiver/amplifier 16 during the time period in which no signals of importance should be occurring.

The echo received pulse 25 from the receiver/amplifier 16 is supplied to the pulse receiver 18. The pulse receiver 18 transforms this signal into a pulse 29, FIG. 2, having a predetermined duration and a fast rise time. The pulse receiver 18 also distinguishes between the signal from the receiver/amplifier which corresponds to the energizing signal, and the signal from the receiver/amplifier 16 which corresponds to the echo pulse 21. In connection with this, the pulse receiver 18, upon receiving an energizing and a corresponding echo signal, transmits a "valid echo" signal indication to sequence control circuit 32 to be described in detail later. This "valid echo" signal is utilized by the sequence control circuit 32 to monitor the sampling process.

The echo signal, which is extracted by the pulse receiver 18, is supplied to an error detector circuit 20. The error detector circuitry 20 implements a method for measuring a time interval by which quantization error, often present in digital measurements, is greatly reduced. In this method, a time interval is measured with respect to a two-phase clock. Preferably, the phase difference between the two clocks is 180 degrees; however, with the proper adjustment, phase differences greater than or less than 180 degrees can be used satisfactorily. A first clock 31 and a second clock 33 are shown in FIG. 2. The second clock 33 is 180 degrees out-of-phase with the first clock 31.

In this method, the time interval is defined to commence upon the instant at which the echo pulse is received. The interval is defined to end upon the occurrence of a selected state within each of the clocks. This selected state can be a rising edge, a falling edge, a zero-crossing or other state of the clock signal. Additionally, the clock state can be further described by designating a numbered occurrence of the particular state, or for example, the first occurrence.

In the preferred embodiment of the present invention, the first rising edge after the receipt of the echo pulse is selected to be the clock state which defines the end of the time interval. Because each clock is 180 degrees out of phase with the other, the rising edge in one clock will occur one-half cycle before or after the rising edge in the other clock. If the longer of the time intervals between the receipt of the echo pulse and the occurrence of the specified state in the clocks is chosen, it can be seen that the time interval involved will always be at least one-half cycle of the clock frequency in length. In turn, because the time interval to be measured has a minimum value, the interpolation error is greatly reduced. In FIG. 2, it can be seen that the time interval corresponding to the second clock signal 33 is the longer interval.

Theoretically, the accuracy by which a particular interval is digitally measured, is determined by the width of the sampling interval used. For example, if the sampling interval were 50 nanoseconds, the quantization error associated with measurements using such a sampling interval is 50 nanoseconds. When an attempt is made to measure the incremental part of the time interval which falls within a sampling interval, the accuracy with which such a measurement can be made decreases as this incremental interval becomes smaller. After a point, this incremental time interval cannot be measured at all. On the other hand, in the present invention, the incremental time period is selected to be at least as large as one-half the sampling period used. As such, the incremental time interval is always large enough so that an accurate measurement can be made.

The output of error detector 20 is a pulse 35, FIG. 2, having an interval corresponding to the larger of the two incremental time intervals. This pulse is supplied to error storage circuit 22 wherein the pulsewidths for a large number of individual samplings are accumulated. This error total is converted into digital form by analog to digital converter (A/D) 40, and is supplied to output registers 24.

Concurrently, with the detection of the above error signal, count control circuit 26, using the second clock 31, FIG. 2, as a reference, controls a count of the number of clock pulses which occur between the insertion of the energizing initiation signal 17, FIG. 2, and the receipt of the echo pulse 21. The count control circuit 26 receives an energizing signal-sent indication from main pulse and blanking circuit 36 to be described in detail later. Upon receipt of this signal, the count control circuit 26 presents a series of pulses from the second clock 33, FIG. 2, to the output register 24. This clock pulse train 39, FIG. 2, is truncated by the count control circuit 26 according to a count-adjust-signal from the error detector 20. This count-adjust signal is necessary because of the two-phase clock method in which the error is determined, as discussed above. Whenever the error is referenced to the second clock 33, the pulse count terminates after the first pulse of the second clock 33, which follows the receipt of the echo signal. It can be seen from examination of signal 41 in FIG. 2 that the pulse count 39, minus the error signal 41 will yield the correct time interval.

On the other hand, when the error is referenced to the first clock 31, as is the error signal 43, in FIG. 2, a straightforward subtraction of this incremental time interval from the corresponding pulse count 39, will yield a time interval which is ½ cycle too small. This ½ cycle error must, therefore, be accounted for in the time interval calculation.

One method of implementing this correction is to add another pulse to the pulse count, every other time the error signal 39 is referenced to the first clock 31. The addition of a pulse to the pulse count corresponds to two extra half-cycles of time over two sample periods. The half-cycle shortfall which arises for each sample period is thereby eliminated.

The "count-adjust-signal" causes the pulse count 39 to terminate two pulses later, on alternate samples, whenever the first clock 31 is used as a reference for the error signal 35 measurement. When the second clock 33 is used as the error signal reference, the "count-adjust signal" causes the count to terminate on the next second clock pulse.

Output registers 24 accumulate the number of pulses being sent over by count control 26. Additionally, for each sample set, the output registers include the error total, which has been converted to digital form in A/D converter 40, from error-storage circuitry 22. Output register 24 supplies this data to the intelligent processing and control means 30, after an interrogate request signal, IRQ, is sent to such intelligent processing and control means 30. This interrogate request signal is sent by the sequence control circuit 32 after a full sample set has been obtained. Register select circuit 28 receives address data from the intelligent processing and control means 30, which it decodes to designate the specific register in output register 24 which is to supply data to the intelligent processing means 30.

The number of samples taken above is controlled by sequence control circuitry 32. Sequence control circuitry 32 receives an interrogation command on line INTE from the intelligent processing and control means 30. This interrogation command initiates a count within sequence control circuitry 32 of a predetermined number of valid samples taken by the time interval measuring means 15. The sequence control 32 outputs the signal on line IRQ to the intelligent processing means 30 to indicate that a valid sample sequence has occurred. In the preferred embodiment of the present invention, a sampling sequence comprising approximately 500 samples has been chosen. A valid sampling sequence is defined to comprise a block of samples which are consecutive and all of which were valid. If a single invalid sample occurred within the block, the count would start anew.

An energizing initiation pulse is supplied by fixed delay 34 to the main pulse and blanking control circuitry 36. Within the main pulse and blanking circuit 36, this initiation pulse triggers an energizing trigger pulse which, when supplied to pulser circuit 14, causes the energizing signal to be supplied to the transducer 12. Fixed delay 34 comprises a means for supplying the initiation pulse at a predetermined periodic interval, which is synchronized to the second clock 33.

Once activated by system power-up, the fixed delay circuit is essentially free-running. It thereafter continuously supplies the initiation pulse to the pulse and blanking circuit 36 on a periodic basis. As such, the pulse-and-blanking circuit 36 will continue to output an energizing trigger pulse until it is told to do otherwise. In the present invention, the count down decoder 139 supplies a reset signal to the pulse-and-blanking control circuit 36 which resets the energizing pulse generating function.

The blanking circuitry contained within pulse and blanking circuit 36 supplies blanking signals to the receiver/amplifier 16. These blanking signals designate a window through which the receiver/amplifier 16 is instructed to monitor the signals being received from the transducer 12. For all time intervals outside the designated windows, the receiver/amplifier 16 will be effectively turned off. These blanking windows are referenced to the point in time at which the energizing initiation pulse is output from the pulse and blanking circuit 36, the point in time in which an echo pulse is received in the pulse receiver 18, and according to blanking data supplied by the intelligent processing means 30. As discussed in connection with the receiver/amplifier 16 above, the blanking windows, or times at which the receiver/amplifier 16 is turned on, are chosen to "open up" just prior to the time a main bang trigger pulse is to be output, and just before the time the first echo signal is expected to occur. These windows are closed upon the output of the energizing signal, and the receipt of an echo signal. Because it is only the initial edge of the various signals which are of interest, and because the energizing and echo signals are potentially multiple and comprise a multitude of frequencies and amplitudes, the use of blanking windows to examine only those intervals of interest greatly enhance the operation of the present invention.

The blanking data supplied by the intelligent processing 30 is received through control and input registers 42. The intelligent processing means 30 derives this blanking data from information which it receives from the user, as well as from information that it has internally. Generally, this blanking data specifies the time interval, following the output of a main bang trigger pulse, after which the echo pulse is expected to be received, for the particular tensil load member undertest. This includes a consideration of the temperature, the material, the length, and other physical parameters involved in the particular sampling circumstances.

The two-phase clocks 31 and 33 are supplied by clock circuit 38. Clock circuit 38 derives these clocks from a crystal oscillator. This crystal oscillator output is enabled according to a reset signal supplied by the intelligent processing means 30.

The intelligent processing means 30, as discussed above, provides control and timing signals to and receives time interval data from the time interval measuring means 15. Basically, the intelligent processing means 30 instructs the time interval measuring means 15 as to when to start a new sampling set, the blanking windows which should be used, the sample quantity to be taken, and the initialization point to which measurements are to be referenced. The intelligent processing means 30 can selectively receive data stored in the output registers 24 of the time interval measuring means 13.

The intelligent processing means also receives information from the user through a data entry means, for example, a keyboard 44. Included in the information received from the user are: bolt specification, including length, type, and grip-length; stress limits; temperature; and display units. The intelligent processing means then evaluates this user supplied information and instructs the time interval measuring means 15 in the actual sampling of the tensil load member under test, as well as in the determination of tensil load member length, and the stress to which the tensil load member is being subjected. The intelligent processing means 30 then provides the user with a visual readout 46 and a hardcopy 48, such as from a printer. Satisfactory visual read-outs include light emitting diode displays and liquid crystal displays.

Contained within the intelligent processing means 30 are tables which contain information on the various tensile load member types specified by the user. Also contained within the tables are quantities which describe the physical properties of the various tensile load members for changes in temperatures and stress.

The stress determination by the intelligent processing means includes the application of the various user-supplied parameters, self-contained table quantities, and measured time intervals, to Hooke's Law. Hooke's Law is given by the equation.

$$S = (\Delta L E / Lg)$$

Where S=stress, $\Delta L$ equals a change in length due to the applied load, E=the modulus of elasticity (which is a function of temperature), and Lg=the grip-length which is that portion of the length of the tensile load member over which the load is actually applied, for example, the distance between the head of a bolt and the position on the bolt where the nut threads accept the applied load is positioned.

The grip-length Lg is supplied by the user. The modulus of elasticity E is calculated according to the equation $E = Eo - C_E(T - 72)$ where Eo=the modulus of elasticity of the particular material and a temperature of 72° F., $C_E$=the coefficient of the modulus of elasticity over temperature, and where T=the actual temperature at which the measurements are being made.

The elongation, or $\Delta L$, is the change in length due to the loading of the tensile load member. This elongation is determined by the intelligent processing means 30 from the time interval data obtained from the time interval measuring means 15.

This time interval data comprises time interval measurements corresponding to the unloaded tensile load member, as well as to the loaded tensile load member. For each set of time interval measurements, the intelligent processing and control means determines a corresponding length. The difference between these lengths then yields the $\Delta L$ or elongation.

The intelligent processing means 30 determines, from the total number of pulses counted in each sampling set, from the clock to which each pulse corresponds, and from the number of samples within each sampling set, the length of the tensile load member. The pulse counts which are supplied to the intelligent processing means 30 by the time interval measuring means 15 comprise the total number of pulses counted, and the digital representation of the sum total of the error signals for the sampling set. The intelligent processing means 30 converts this digital error quantity into an equivalent number of pulses, which is then added to the total pulse count. In the preferred embodiment of the present invention, the pulse count is used directly to determine the length of the tensile load member, both in its unloaded state and under stress, taking into account velocity differences due to temperature and stress effects. Alternatively, the pulse count could be converted into a time interval which, in turn, could be applied to the velocity of an ultrasonic wave in a particular material to derive an equivalent length.

The actual operations performed upon the data are shown in more detail in Appendix A attached. In general, these operations take into consideration the additional length of the tensile load member due to expansion from temperature change, the fact that an ultrasonic shock wave travelling in a particular type of material will have a velocity which is a function of temperature, and that the velocity of a shock wave travelling in materials under stress will differ as a function of the amount of stress to which the material is subjected. Additionally, because a tensile load member can have several regions of different stress, corrections in the sonic velocity factor used should be made accordingly. The detailed operations performed by the intelligent processing means 30 to derive the length and stress information are described in Appendix A.

Referring more particular to FIGS. 3 and 4, the preferred embodiment to the present invention will now be described in greater detail.

FIGS. 3 and 4 are simplified schematics of the preferred embodiment of the present invention. In this preferred embodiment, the intelligent processing means 30 includes a microcomputer 110. The first clock reference signal is referred to as oscillator 1 and the second clock reference signal is referred to as oscillator 2. As used below, the terms PUP1 and PUP2 refer to pull-up voltage 1 and pull-up voltage 2, respectively. RST 1 refers to the initialization signal which is supplied to the time interval measuring means 15 by the intelligent processing means 30 when the full system is sought to be initialized. In the pulser circuit 14, a capacitor 100 is charged to a very high voltage through resistor 102. One end of capacitor 100 is connected to an output series resistor 104 and one end of resistor 102. The other end of resistor 102 is connected to the high voltage supply. The other end of output resistor 104 supplies to the output of the pulser circuitry 14. The other end of capacitor 100 is connected to the anode of a silicon controlled rectifier (SCR) 106. The cathode of the SCR 106 is connected to ground, while the gate receives the input to pulser circuitry 14. Resistor 108 is connected between the junction of capacitor 100 and the anode of SCR 106, and ground. In operation, the capacitor 100 is charged through a high voltage through resistor 102 and is discharged through the SCR 106. This discharging of capacitor 100 causes a large negative-going spike to be output through resistor 104. This is the energizing signal 19, FIG. 2, which is applied to the transducer 12. The SCR 106 is activated to discharge capacitor 100 through the application of an appropriate signal to a gate. This gating signal is the energizing trigger signal 17, FIG. 2, supplied from the main pulse and blanking circuit 36.

The generation of the energizing pulse which is supplied to the transducer 12 will now be described in greater detail. The energizing pulse results from the interaction of the pulser circuitry 14, the main pulse and blanking circuitry 36, and the fixed delay circuitry 34. As described previously the fixed delay circuit 34 supplies an initiation pulse at a predetermined periodic interval. Referring to FIG. 3, one circuit for generating this pulse is shown.

D flip flop 110 is clocked by oscillator 1, and reset by the inverted output of D flip flop 112. The noninverted output of D flip flop 110 is connected to the input of D flip flop 112 through OR gate 114. OR gate 114 also receives the noninverted output of D flip flop 112. D flip flop 112 is clocked by oscillator 2, and reset by the output of counter 116. Counter 116 is iterated by a signal supplied by AND gate 118. The signal supplied by AND gate 118 corresponds to that of oscillator 2 whenever the output of D flip flop 112 is high.

The inverted output of D flip flop 110 is connected to the load input of counter 116. In this manner, whenever the inverted output of D flip flop 110 is low, the counter 116 will be instructed to re-initialize its count. In the preferred embodiment of the present invention, the counter 116 is initialized to start its count from zero, and presents an output pulse to D flip flop 112 when 500 pulses have been counted.

In operation, the initialization signal RST 1 is supplied to the input of D flip flop 110 upon initialization of the system by the intelligent processing means 30. In synchonization with oscillator 1, a high level is shifted to the non-inverted output of D flip flop 110. This high level in turn is input, through OR gate 114 to D flip flop 112. This high level is shifted to the non-inverted output of D flip flop 112 in synchonization with oscillator 2. This shifting of a high level to the non-inverted output of D flip flop 112 causes the inverted output to go low. This in turn re-sets D flip flop 110. At this point D flip flop 112 remains at a high state because the high level at the output of D flip flop 112 is reinserted into the input D flip flop 112 through OR gate 114.

When the non-inverted output of D flip flop 112 goes high, AND gate 118 applies the oscillator 2 signal to the count up input of counter 116. At this point, counter 116 has already been initialized to zero by the resetting of D flip flop 110 above. Counter 116 then proceeds to count 500 cycles of oscillator 2, after which time it resets D flip flop 112. This resetting of D flip flop 112 causes a zero to be output from the non-inverted output of D flip flop 112 which in turn causes the oscillator 2 clock pulse to be removed from the count up input to counter 116. Counter 116 is thereby disabled.

The resetting of D flip flop 112 by the counter 116 also causes a high level of be output from the inverted output of D flip flop 112. Up until this point, D flip flop 110 had been disabled. The application of a high level to the reset input of D flip flop 110 permits the non-inverted output of D flip flop 110 to assume a high level on the next oscillator 1 clock pulse. This in turn causes the non-inverted output of D flip flop 112 to go high, which in turn starts the count in counter 116 anew.

The signal which is present at the non-inverted output of D flip flop 110 is therefore shaped by the non-inverted output of D flip flop 112. Whenever the non-inverted output of D flip flop 110 goes high, D flip flop 112 will cause D flip flop 110 to be reset ½ clock pulse cycle later. In the preferred embodiment of the present invention, this interval is 50 nsec. This is because the frequency of oscillator 1 and oscillator 2 is selected to be 10 MHz. Because oscillator 1 is 180 degrees out of phase of oscillator 2, the high level which is present at the non-inverted output of D flip flop 110 will be shifted into D flip flop 112 50 nsec later. As such, 50 nsec will have elapsed from the time the non-inverted output of D flip flop 110 attained a high level to the time that the inverted output of D flip flop 112 assumes a zero level and thereby resets D flip flop 110.

The non-inverted output of D flip flop 110 is connected to the clock input of D flip flop 120 within the main pulse and blanking circuit 36. The signal which is present at the non-inverted output of D flip flop 110 is the energizing initiation signal discussed above.

The main pulse and blanking circuit 36 supplies the energizing trigger signal to the pulser circuit 14, as well as blanking signals to the receiver/amplifier circuit 16. The derivation of the energizing trigger signal will now be discussed. D flip flop 120 is clocked by the energizing initiation signal from the fixed delay circuit 34. The input to the D flip flop 120 is held high by PUP2, or pull-up voltage 2. For each positive going edge which is presented to the clock input of D flip flop 120, a high level output is presented at the non-inverted output of D flip flop 120. The non-inverted output of D flip flop 120 is connected to the input of D flip flop 122 through OR gate 124. The non-inverted output of D flip flop 122 is also routed back to the input of D flip flop 122 through OR gate 124. The inverted output of D flip flop 122 is connected to the reset input of D flip flop 120. The clock to D flip flop 122 is supplied by oscillator 2.

For each energizing initiation signal from the fixed delay circuit 34, D flip flop 120 presents a high level at its non-inverted output. This high level is in turn clocked into D flip flop 122 in synchronization with oscillator 2. When the high level is clocked into D flip flop 122, the low level which is presented at the inverted output of D flip flop 122 causes D flip flop 120 to be reset. D flip flop 120 is now ready to receive the next energizing initiation signal from fixed delay circuit 34. The non-inverted output of D flip flop 120 is thereby caused to go to a low level. The non-inverted D flip flop 122 is kept at a high level because of the connection of the D flip flop 122 input to its output through OR gate 124. The non-inverted output of D flip flop 122 will remain high until the flip flop is reset by a reset signal supplied from clock circuitry 38 count-down decoder 139.

When the inverted output of D flip flop 122 goes low, NAND gate 126 outputs a high level to the gate of SCR 106 in pulser circuitry 14. This is the energizing trigger signal. This causes SCR 106 to discharge capacitor 100. In this manner, the transducer is supplied with the energizing pulse.

In the preferred embodiment of the present invention, the reset signal from decoder circuit 139 to D flip flop 122 occurs approximately 1 microsecond after D flip flop 120 is reset, i.e. one microsecond after the energizing trigger signal has been sent. Decoder circuit 139 includes a preset counter which is enabled whenever an energizing pulse is sent. When the present count has counted down to zero, the decoder circuit 139 outputs the reset signal to D flip flop 122.

In the preferred embodiment of the present invention, the energizing trigger signal therefore has a pulse width of approximately 1 microsecond and is triggered by the energizing initiation signal from the fixed delay circuit 34.

The blanking function of main pulse blanking circuit 36 provides blanking signals to the receiver/amplifier 16, in order to designate the windows through which the time interval measuring means 15 will examine the waveforms from the transducer 12. The clock input of D flip flop 128 is connected to the non-inverted output of D flip flip 122 through OR gate 130. In this manner whenever the non-inverted output of D flip flop 122 is goes into a high level the non-inverted output of D flip flop 128 will go to a high level.

OR gate 130 also accepts a signal from the control and input circuit 42. This signal is inverted by inverter 132. This signal is generated according to information supplied by the intelligent processing means 30, and represents the interval in time after which an echo signal is expected to occur.

The non-inverted output of D flip flop 128 is connected to the input of D flip flop 134 through AND gate 136. The other input of AND gate 136 is supplied from pulse receiver circuitry 18. The level out of AND gate 136 is clocked into D flip flop 134 in synchronization with oscillator 2. A low level will appear at the inverted output of D flip flop into D flip flop 134 in synchronization with oscillator 2. A low level will appear at the inverted output of D flip flop 134 whenever the non-inverted output of D flip flop 128 and the signal from pulse receiver 18 are both high. If either of the above signals are low, a high level will be clocked to the inverted output of D flip flop 134. The inverted output of D flip flop 134 is connected to the reset input of D flip flop 128. D flip flop 128 will therefore be reset whenever a low level is present at the inverted output of D flip flop 134.

The inverted output of D flip flop 128 is supplied through inverter 138 to the AGC input of receiver/amplifier circuitry 16. Whenever a high level is presented to this AGC input, receiver/amplifier circuitry 16 will be turned on. Whenever a low level is presented to the AGC input the receiver/amplifier 16 will turn off. Therefore, whenever the inverted output of D flip flop 128 is low, the receiver/amplifier 16 will be turned on, whereas whenever the inverted output of D flip flop 128 is high, the receiver/amplifier circuitry 16 will be turned off.

In operation, the signals into the clock input of D flip flop 128 cause the inverted output of D flip flop 128 to go low so that inverter 138 presents a high level to the AGC input of receiver/amplifier circuitry 16. These signals open the window by which the receiver/amplifier circuit 16 examines the signals from transducer 12. The signals into AND gate 136 close the window. This is because whenever a high level is output from AND gate 136, a high level is presented to the non-inverted output of D flip flop 134 in synchronization with oscillator 2. This in turn causes the inverted output of D flip flop 134 to assume a low level. This in turn causes D flip flop 128 to be reset so that the inverted output of D flip flop 128 goes to a high level and the level presented to the AGC input of receiver/amplifier circuitry 16 goes low, which causes the window to close.

AND gate 136 presents a high level to D flip flop 134 whenever a high level is received from pulse receiver circuitry 18, and whenever the non-inverted output of D flip flop 128 is high. Thus it can be seen that the energizing trigger circuitry causes the window on the receiver/amplifier circuitry 16 to open, as does the intelligent processing means signal supplied through inverter 132. In turn, the receipt of an energizing signal, or an echo signal from the transducer, as processed by the pulse receiver, will cause the window to close. The signal from pulse receiver 18 is high whenever an energizing pulse or an echo pulse has been received from the transducer 12.

These windows 27a and 27b are shown in FIG. 2, in blanking signal 27. The rising edge of blanking signal 27a corresponds to the receipt of a high level from D flip flop 122. The falling edge of blanking signal 27a corresponds to the receipt of a high level at the input to AND gate 136 from pulse receiver circuitry 18. The rising edge of blanking 27b corresponds to the receipt of a low level from control and input circuitry 42, which indicates that the point in time has been reached at which it is expected that an echo pulse will occur. The falling edge of blanking signal 27b corresponds to the acutal receipt of the echo signal by pulse receiver 18, the receipt of the signal causing a high level to be presented by pulse receiver 18 to AND gate 136.

Referring to FIG. 3, the receipt and processing of signals from the transducer 12 will now be discussed. Receiver/amplifier circuitry 16 comprises a signal conditioning stage, an amplifying stage, and a level shifting stage. In the signal conditioning stage, a signal from transducer 12 is received by one end of capacitor 140. The other end of capacitor 140 is connected to one end of resistor 142, the anode of diode 144, the cathode of diode 146, and the input to the amplifier stage 148. The other end of resistor 142 is connected to ground, as are the cathode of diode 144 and the anode of diode 146. The combination of capacitor 140 and resistor 142 provides a high pass filtering function thereby blocking DC voltages while allowing high frequency transients to pass. Diodes 144 and 146 provide a clamping of the levels which are presented to the amplifier section 148, to less than a few volts peak to peak. This clamping is provided because of the great difference in signal amplitudes received from the transducer 12. For example, the signal from the transducer 12 which corresponds to the energizing signal can have levels of many tens of volts, whereas, the levels corresponding to the echo pulse are more on the order a few tenths of volts.

This clamped input signal is supplied to the amplifier stage 148. The amplifier stage comprises a high frequency amplifier capable of handling transients in the nanosecond rise-time range. The amplifier section also has an automatic gain control (AGC) which permits the amplifier to be turned on and off. As discussed above, the AGC input is supplied by a blanking signal from the main pulse and blanking circuitry 36.

The output of the amplifier stage is supplied to the level shifting stage. Capacitor 150 connects the output of amplifier 148 to the junction of resistors 152 and 154. The other end of resistor 152 is connected to ground while the other end of resistor 154 is connected to the base of transistor 156. The emitter of transistor 156 is connected to ground, while the collector of transistor 156 is connected to one end of resistor 158 and to the input of pulse receiver 18. The other end of resistor 158 is connected to a DC supply voltage of approximately 4.5 volts. In response to signals from amplifier 148, the level shifting circuitry output a signal which varies between zero and 4.5 volts to the pulse receiver circuitry 18.

This level shifted output is received by a Schmidt trigger circuit 160 in pulse receiver circuit 18. These circuits "square-up" the received signal to provide a sharp rising edge to a receiver circuit 162. The receiver circuit 162 is a retriggerable "one shot" multivibrator which outputs a single pulse of variable width depending upon the number of pulses from the Schmidt trigger 160. In the preferred embodiment of the present invention, this pulse width is approximately 6 microseconds or longer. The output of the receiver 162 provides signal levels which govern the closing of the window produced in the blanking circuitry 36 as discussed above. The pulse duration of the receiver 162 output is chosen to be sufficiently long to prevent any transients following the initial rising edge of the signals received from receiver/amplifier circuitry 16, from causing any change in the output of the receiver circuitry 162. In this manner, any unwanted signal transients are rejected. In operation then, the receiver circuit 162 outputs a high level to the blanking circuit 36 whenever an energizing signal or an echo signal is received by the receiver/amplifier circuitry 16 from the transducer circuitry 12.

The output of receiver 162 is also connected to the clock inputs of D flip flop 164 and D flip flop 166. The input of D flip flop 164 is connected to PUP2. A high level is therefore provided at its non-inverted output whenever the receiver circuit 162 presents a rising edge to the clock input of D flip flop 164. The input of D flip flop 166 is connected to the non-inverted output of D flip flop 164. Both flip flops are reset by a low level from the inverted output of D flip flop 120 in the main pulse and blanking circuitry 36. Recall that the inverted output of flip flop 120 goes to a low level whenever a pulse is received at the clock input of D flip flop 120 from the fixed delay circuitry 24. This corresponds to the energizing trigger signal. Therefore D flip flops 164 and 166 are both reset whenever the energizing initiation signal is produced. As such, for every cycle of energizing/echo signal produced the, the operation of D flip flop 164 and 166 are reset to start a new.

In operation, the first clock of the new cycle received by D flip flop 164 corresponds to the energizing signal. Because D flip flop 164 and 166 have both been reset prior to the reception of this energizing signal clock, the non-inverted output of D flip flop 164 will be low, and this low level will be clocked into D flip flop 166 by the energizing signal. This energizing signal also causes a high level to be presented at the non-inverted output of D flip flop 164. This high level is then clocked into D flip flop 166 upon the reception of the next clock pulse, or the echo clock pulse. The non-inverted output of D flip flop 166 will therefore assume a high level only after two consecutive pulses are received from the transducer 12 during the current energizing/echo signal interval.

The non-inverted output of D flip flop 166 is supplied to the input of D flip flop 168, as well as to error detecting circuitry 20. D flip flop 168 provides count adjusting signals to sequence control circuitry 26 as well as to error storage circuitry 22.

The non-inverted output of D flip flop 166 represents the point in time at which the echo signal is designated as being received. See signal 29 in FIG. 2. It can be seen from FIG. 2 that the duration of this signal 29 extends until the next energizing initiation signal is generated. This is to prevent secondary reflection signal received from the transducer 12 from affecting the processing in the time interval measuring means 15.

The error detecting circuitry 20 receives the non-inverted output of D flip flop 166 through the clock inputs of D flip flops 170 and 172. Recall that the error detecting circuitry 20 measures the time interval between the designated receipt of the echo pulse, and a specified state of the reference oscillators oscillator 1, and oscillator 2. The input to D flip flop 170 is connected to PUP2 as is the input to D flip flop 172. The non-inverted output of D flip flop 170 is connected to the input of D flip flop 174. The non-inverted output of D flip flop 172 is connected to the input of D flip flop 176. The clock input of D flip flop 174 is connected to oscillator 2 whereas the clock input to D flip flop 176 is connected to oscillator 1.

In the preferred embodiment of the present invention, the reference clock states which are used to designate the end of the error interval are chosen to be the rising edge of each clock. Therefore, D flip flop 174 and D flip flop 176 are chosen to be responsive to to the rising edge of oscillator 2 and oscillator 1 respectively. The inverted output of D flip flop 174 is connected to the reset input of D flip flop 170, while the inverted output of D flip flop 176 is connected to the reset input of D flip flop 172. It can be seen therefore that when the non-inverted output of D flip flop 166 goes high, a high level is presented at the non-inverted outputs of D flip flop 170 and D flip flop 172. This high level will not be clocked into the non-inverted output of D flip flop 174 until oscillator 2 presents a rising edge to the clock input. The same applies to D flip flop 176, that is, until oscillator 1 presents a rising edge to the clock input of D flip flop 176, the high level present at the input to D flip flop 176 will not be shifted to its non-inverted output. Because oscillator 2 is 180 degrees out of phase from oscillator 1, the point in time at which the non-inverted outputs of D flip flops 174 and 176 will assume a high level will differ by ½ clock cycle. This means that D flip flop 176 will be reset ½ clock cycle before or after D flip flop 174 is reset. When D flip flops 170 and 172 are reset, their non-inverted outputs assume a low level.

The signal at the non-inverted output of D flip flop 170 therefore represents the time interval between the receipt of the echo signal, and the first rising edge of oscillator 2 which is subsequent thereto. The signal at the non-inverted output of D flip flop 172 therefore corresponds to the time interval representing the time between the receipt of the echo pulse, and the first rising edge in the oscillator 1 waveform which is subsequent thereto. These two outputs are then applied to OR gate 178. The output of OR gate 178 will therefore go high when either D flip flop 170 or D flip flop 172 are high, and remain high so long as either D flip flop 170 or D flip flop 172 is high. Therefore the output of OR gate provides the longer of the two error time intervals measured. This error signal is supplied to error storage circuitry 22 for use in obtaining the average error over a large number of samples.

In order to compensate for the use of oscillator 1 or oscillator 2 as a reference in calculating the total pulse count, additional circuitry is provided as follows. AND gate 180 receives as input the inverted output of D flip flop 170 and the non-inverted output of D flip flop 172. The output of AND gate 180 is applied to the clock input of D flip flop 182. NAND gate 184 receives as inputs the non-inverted output of D flip flop 170 and the inverted output of D flip flop 172. The output of NAND gate 184 is applied to the reset input of D flip flop 182. The input to D flip flop 182 is tied to PUP2.

As connected, a high level is shifted to the non-inverted output of D flip flop 182 whenever D flip flop 170 has been reset by D flip flop 174, and at the same time, the non-inverted output of D flip flop of 172 is high. The clock input to D flip flop 182 is responsive to a rising edge. Therefore, the point at which D flip flop 170 is reset by D flip flop 174 will determine the point in time in which a high level will be shifted to the non-inverted output of D flip flop 182. If on the other hand, D flip flop 172 is reset before D flip flop 170, no clock pulse will be presented to D flip flop 182.

A reset signal is supplied from NAND gate 184, and occurs on the falling edge of the signal. This falling edge is presented to the reset input of D flip flop 182 whenever there is a transition from a state in which either the non-inverted output of D flip flop 170 or the inverted output of D flip flop 172 is low, to a state in which both the non-inverted output of D flip flop 170 and the inverted output of D flip flop 172 are high. This occurs whenever D flip flop 172 is reset before D flip flop 170. This corresponds to the case where the error time interval, which is referenced to oscillator 2, is longer than the error time interval which is referenced to oscillator 1.

The non-inverted output of D flip flop 182 is therefore clocked to a high level whenever the time interval referenced to oscillator 1 is longer than the time interval referenced to oscillator 2, and is reset whenever the time interval referenced to oscillator 2 is longer than the time interval referenced to oscillator 1. NAND gate 186 is supplied with the non-inverted output of D flip flop 182 and with the non-inverted output of D flip flop 172. The output of NAND gate 186 is supplied to the clock input of D flip flop 188. The inverted output of D flip flop 188 is connected to the input of D flip flop 188. In this configuration, the non-inverted output of D flip flop 188 alternates between a high and a low level with each successive clock pulse from NAND gate 186. The output of NAND gate 186 provides the required positive going transition whenever there is a transition from a state in which the non-inverted output of D flip flop 172 is high and the non-inverted output of D flip flop 182 is high, to the state when either one of them is low. This occurs whenever the error time interval referenced to oscillator 1 is longer than the time interval referenced to oscillator 2.

The non-inverted output of D flip flop 188 is supplied to count control circuitry 26. This output alternates between a high and a low level whenever the error time interval referenced to oscillator 1 is longer the error time interval referenced to oscillator 2. In this manner an indication is provided to the count control circuitry 26. This, in turn, is used to subtract a clock pulse from the pulse counting function to adjust for the use of a difference reference signal in the pulse count, as described above.

The actual process by which a pulse is subtracted from a pulse count is implemented in count control circuitry 26. NAND gate 190 receives inputs from the non-inverted output of D flip flop 182, from the non-inverted output of D flip flop 172, as well as the signal from the non-inverted output of D flip flop 188. NAND gate 192 receives the same inputs as does NAND gate 190, except that the non-inverted output of D flip flop 176 is substituted for the non-inverted output of D flip flop 172. NAND gate 194 receives an input from the inverted output of D flip flop 182 as well as from the non-inverted output of D flip flop 174. The outputs of NAND gate 190, 192, and 194 are connected together and supplied to the input of D flip flop 196. A pull-up resistor 191 is connected between the input to D flip flop 196 and positive voltage. D flip flop 196 is set by a signal originating from the main pulse and blanking circuitry 36, and in particular from the non-inverted output of D flip flop 120. In this manner, the non-inverting outputs of D flip flop 196 are set to a high level whenever an energizing trigger signal is output from the main pulse and blanking circuitry 36. The clock input to D flip flop 196 is supplied from the output of AND gate 198. The inputs to AND gate 198 are supplied from oscillator 1 and the non-inverted output of D flip flop 196. Therefore whenever the non-inverted output of D flip flop 196 is high, AND gate 196 permits the oscillator 1 frequency to pass through and be applied to the clock input of D flip flop 196. On the other hand, when the non-inverted output of D flip flop 196 is low, no clock pulse is permitted to pass to the clock input of D flip flop 196.

The non-inverted output of D flip flop 196 is supplied to the input of NAND gate 200. The other input to NAND gate 200 is supplied from oscillator 2. Whenever the non-inverted output of D flip flop 196 is high, NAND gate 200 permits the oscillator signal to pass through. The set signal from main pulse and blanking circuit 36 initializes the non-inverted output to a high level which causes NAND gate 200 to permit oscillator 2 pulses to pass. The timing of the insertion of a zero level into the input of D flip flop 196 by NAND gates 190, 192 or 194 determines the number of pulses which will be permitted to pass through NAND gate 200 during a particular sample period.

NAND gates 190, 192, and 194 examine the states of the circuitry within error detector circuit 20 and cause a low level to be inserted into the input of D flip flop 196 whenever the error time interval referenced to oscillator 2 is longer than that for oscillator 1 and at the instant D flip flop 182 is reset. This point in time corresponds to the end of the oscillator 2 error interval. Additionally, a low level will be inserted into the input of D flip flop 196 whenever the error interval referenced to oscillator 1 is longer. However, in this case, the low level will be inserted an additional clock cycle later, on every other sample which is referenced to oscillator 1.

The output of NAND gate 200 is supplied to the "count-up" clock input of a counter 202, found in FIG. 4. Counter 202 accumulates the pulse count corresponding to all of the samples taken within a sample set.

Returning to FIG. 3, the error storage circuit 22 will now be discussed. The error time intervals supplied from OR gate 178, of the error detector circuitry 20, is applied to one end of resistor 204 and to the anode of diode 206. The other end of resistor 204 is connected to a positive voltage, while the cathode of diode 206 is connected to capacitor 208, the input to error amplifier 210, and to the output of NOR gate 212.

The error time interval supplied by OR gate 178 causes capacitor 208 to charge toward the positive voltage through resistor 204 and diode 206. The time interval corresponding to the error signal from OR gate 178 determines the voltage to which capacitor 208 will be charged. When the output of OR gate 178 returns to zero, diode 206 prevents the capacitor from being discharged. In this manner, the voltage on capacitor 208 is maintained for later sampling by analog to digital (A/D) converter 40, through error amplifier 210, or for receiving additional voltage which corresponds to the next sampled error interval. Amplifier 210 is a high input impedance, high gain amplifier the output of which is connected to the input of an A/D converter 40.

The connection of capacitor 208 to the output of NOR gate 212 is provided to permit the capacitor 208 to be discharged whenever a new set of samples is sought to be taken. NOR gate 212 discharges capacitor 208 whenever the intelligent processing means 30 provides a positive going interrupt signal through sequence control circuitry 32, or whenever the non-inverted output of D flip flop 168, in pulse receiver circuitry 18, goes high. In the latter case, this positive going wave form represents the case where an energizing initiation signal has been sent before the echo signal flip flop 166 has been reset. This condition corresponds to an invalid sampling sequence.

In sequence control circuitry 32, an interrupt signal is received from the intelligent processing means 30, and an interrupt-request signal is provided to the intelligent processing means 30. The interrupt signal coming from intelligent processing means 30 is received by the clock input of D flip flop 214, and inverter 216. This causes the non-inverted output of D flip flop 214 to assume a high level. This high level is applied to the input of D flip flop 218, and is clocked to the non-inverted output of D flip flop 218 just prior to the occurence of the next energizing trigger pulse, from the fixed delay circuitry 34. When the non-inverted output of D flip flop 218 assumes a high level, this high level is presented to the input of D flip flop 220, through OR gate 222. This high level is then clocked to the non-inverted output of D flip flop 220 in synchronization with oscillator 1. The non-inverted output of D flip flop 220 is connected to the input of OR gate 222 and to an input of AND gate 224. The connection to the input of OR gate 222 permits the non-inverted output of D flip flop 220 to remain high even after the non-inverted output of D flip flop 218 has assumed a low value. AND gate 224 controls the count sequence in counter 226, by which it is determined whether a sufficient number of samples have been taken to constitute a valid and complete sample set.

Counter 226 is preset to count from zero upon a load signal from the inverted output of D flip flop 218. The output of AND gate 224 is connected to the count-up input of counter 226, and will initiate the count whenever the non-inverted output of D flip flop 220 is high, and a high level is supplied OR gate 228. OR gate 228 will supply a high level whenever the inverted output of D flip flop 168 is high and the non-inverted output of D flip flop 120 is high; or whenever the non-inverted output of D flip flop 168 is high and either the non-inverted output of D flip flop 170 is high or the non-inverted output of D flip flop 172 is high. In other words, a valid sampling is deemed to occur whenever an energizing initiation signal is being generated and D flip flop 168 is not in the reset mode, or, whenever D flip flop 168 is in the reset mode and either D flip flop 170 or D flip flop 172 has received an echo signal received indication from pulse receiver 18.

In this manner, a count-up signal is supplied to counter 226 for each sample taken, and wherein each sample represents the reception of an energizing pulse and an echo pulse.

When counter 226 has reached its intended count, D flip flop 220 is reset through AND gate 230. This resetting of D flip flop 220 causes the inverted output of D flip flop 220 to assume a high level which in turn causes D flip flops 218 and 214 to reset. Additionally, this causes a high level to be clocked to the non-inverted output of D flip flop 232. This causes the counter 226 to be cleared. The inverted output of D flip flop 232 is supplied to the enable input of A/D converter 40. This instructs the A/D converter to sample the voltage present on capacitor 208 and to convert such analog voltage into an equivalent digital word.

The output of inverter 216 is supplied to the clock input for D flip flop 234. The input to D flip flop 234 is supplied from PUP2, therefore a high level is shifted to the non-inverted output of D flip flop 234 in response to a positive going output from inverter 216. This positive going output from D flip flop 234 causes D flip flop 232 to reset, as well as provides an interrupt request signal through OR gate 236, to the intelligent processing means 30.

Referring now to FIG. 4, output register circuitry 24 will now be described. Output register 24 receives the output from A/D converter 40, and stores it in latch 238. The pulse-count from NAND 200 is applied to the count-up input of counter 202. The counter 202 output is supplied to latch 240 where it is held until required by the intelligent processing means 30. Address decoding circuit 28 receives address data from the intelligent processing means 30 and decodes such data to enable specified latches, for example, latch 240, 238, or 242.

Latch 242 in control and input circuitry 42, receives blanking interval data from intelligent processing means 30. This blanking interval data is then applied to preset a counter 244. The clock for counter 244 is supplied from count control circuitry 26. More specifically, D flip flop 246 receives a clock signal from D flip flop 122 in the mainpulse and blanking circuit 36. The input of D flip flop 246 is connected to PUP2 and the non-inverted output of D flip flop 246 is connected to AND gate 248. The other input to AND gate 248 is connected to oscillator 1. The reset input of D flip flop 246 is connected to the output of counter 244, in control and input circuitry 42 through inverter 250.

Whenever an output is generated from counter 244, D flipflop 246 is reset. This in turn causes the non-inverting output of D flip flop 246 to assume a low level, which in turn prevents oscillator 1 from passing through AND gate 248. This in turn disables the clock input to the count-down input of counter 244 which halts the count.

The countdown clock is reapplied through AND gate 248 whenever a positive going level is presented to the clock input of D flipflop 246 from the non-inverted output of D flip flop 122. In other words, whenever an energizing initiation signal is generated, the countdown clock to counter 244 is enabled. Counter 244 counts down from the preset number supplied by the intelligent processing means 30 and outputs a high level when the count has reached zero. This high level is then received by inverter 132 of the main pulse and blanking circuit 36 which in turn causes the window in the receiver/amplifier circuit 16 to open up in anticipation of the reception of the echo pulse.

The preset value supplied by the intelligent processing means 30 to counter 244 is an estimate of the amount of time required for the echo signal to be received once an energizing signal is output. This estimate is a function of the length of the tensile load member, the material, the temperature, and the stress applied, for example.

For the preferred embodiment of the present invention, clock circuitry 38 is referenced to a 20 MHz crystal controlled clock. This clock is divided by two and shifted in phase by 180 degrees to produce oscillator 1 and oscillator 2 reference frequencies. These reference frequencies are thereafter supplied to the time interval measuring means 15. The clock circuitry 38 is initialized by a reset signal from the intelligent processing means 30.

FIG. 5 is a flow diagram illustrating the interaction between the intelligent processing and control means 30 and the time interval measuring and control means 15. After the power-up step 300, the intelligent processing means 30 initialize internal circuitry and then proceed to obtain data from the user, step 302. Included in this data are the operating temperature, the units in which the stress measurements are to be displayed, the group with which the particular tensile load member is associated, the type of the tensile load member within the associated group, the approximate length of the tensile load member, the stress limits upon the occurrence of which the user is to be notified, the reference number of the particular tensile load member under test, and the grip length. In step 303, the intelligent processing and control means 30 retrieves user data from memory for processing.

Based upon the above user-supplied data, the intelligent processing means determine the approximate amount of time required for the pulse echo signal to be received by the transducer, following the insertion of an energizing signal into the tensile load member under test, step 304. In step 306, the intelligent processing and control means 30 supply this time interval blanking data to the time interval measuring means 15. The data are loaded into control and input circuitry 42. This blanking data is thereafter available to the time interval measuring means 15 throughout the sampling process for the particular tensile load member under test.

After blanking data have been supplied in step 306, the intelligent processing and control means 30 initiate the actual sampling process by the time interval measuring means 15, by sending an interrupt enable signal to the sequence control circuit 32, step 312. In step 310, the intelligent processing and control means 30 determine whether an interrupt request signal, IRQ, has been received from the time interval measuring means 15. Until such IRQ signal has been received, the intelligent processing and control means 30 proceed through step 314 and back to step 310 in a "wait" loop. Recall that the IRQ signal from the time interval measuring means 15 indicates that a valid and complete sample set has been obtained.

In step 318, the intelligent processing means send address data to the output register select circuit 28, which, in turn, causes the error count to be read from output register 24, and from pulse count register 24. This pulse count and error data are then utilized in step 320 to determine the length and stress quantities for the particular tensile load member. These quantities are then displayed and output to the user in step 322. Step 324 compares the measured stress quantity against the user-supplied stress limits. If an over-limit is observed, the intelligent processing means sound an alarm, step 326. If no over-limit is observed, the intelligent processing means proceed to step 314 in which it is determined whether a new test and tensile load member are to be processed, or whether the current sampling operation is to continue. If a new test is to be initiated, the intelligent processing means return to step 303 in which user data is retrieved as described above.

In operation, the unstressed length of the tensile load member is first obtained. This is followed by a determination of the stressed length of the tensile load member, compensated for temperature, sonic velocity variations, tensile load member material effects on sonic velocity, and other physical parameter effects upon the elongation measurement. The length and stress quantities are then determined by the intelligent processing means according to the equations described in Appendix A.

As the user applies increasing load to the tensile load member, the intelligent processing means initiate new sample sets by the time interval measuring means, obtains data from those new sample sets, determines the updated length and stress quantities, and displays those quantities to the user. In this manner, the user has immediate and on-going indications of the conditions to which the tensile load member under test is being subjected. In this manner, the user can also adjust the tensile load member to the exact stress or elongation quantity desired.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention claimed.

APPENDIX A

Pulses, PL, for a single tensile load member length:

$$PL = \frac{P}{2N} - \frac{KD}{2} - KP1 - \frac{ERRCNT}{KP2}$$

where, P = total pulse count obtained, for the full sample set, from output registers 24.
N = total number of samples in a sample set.
KD = Constant, inherent system delay.
KP1 = Constant to adjust for pulse counting technique.
ERRCNT = Error count, in digitized form, from output registers 24.
KP2 = Constant to convert digitized word into an equivalent average pulse quantity per sample.

Temperature Differential, T, from 72° F.

$$\Delta T = T - 72$$

where, T = Temperature during test, degrees F.

Modulus of Elasticity, $E_T$, at T $$E_T = E_0 - C_E \Delta T$$

where, $E_0$ = Nominal elasticity of the material at 72° F.
$C_E$ = Coefficient of elasticity as a function of temperature Coefficient of Thermal Expansion, $A_T$, at T $$A_T = A_0 - C_A \Delta T$$

where, $A_0$ = nominal coefficient of thermal expansion, for the particular tensile load member material
$C_A$ = Coefficient of the coefficient of thermal expansion, for T Sonic velocity, $V_T$, at T, for the given tensile load member material $$V_T = V_0 - C_T \Delta T$$

where, $V_0$ = sonic velocity in the tensile load member material at 72° F.
$C_T$ = Coefficient of sonic velocity as a function of temperature Length of unstressed bolt, $L_0$, at T $$L_0 = \frac{PLV_T}{1 + A_T \Delta T}$$

Elongation, ELONG, at T $$ELONG = \frac{V_T PL - L_O - A_T L_O \Delta T}{1 + \frac{KE_T PL}{L_g} - \frac{KE_T L_O}{L_g V_T} + \frac{KE_T}{V_T} - \frac{KE_T L_O A_T \Delta L}{L_g V_T}}$$

where, K = Coefficient for sonic velocity vs. stress, for the particular tensile load member material
$L_g$ = Grip length, approximate, for the particular application Stress, STRESS, on tensile load member $$STRESS = \frac{ELONG \times E_T}{L_g}$$

What is claimed is:

1. An apparatus, for measuring the length and stress in a tensile load member, wherein a transducer is energized to insert an ultrasonic pulse into one end of the load member and the transducer receives an ultrasonic pulse echo which is reflected back to the transducer from the other end of the load member, the transducer converting the echo into an equivalent electrical signal, the apparatus comprising time interval measuring means for obtaining elapsed time data corresponding to the interval between the energizing of the transducer and the receipt of the pulse echo;

intelligent processing and control means which receive the elapsed time data and user supplied information for controlling the time interval measuring means and for deriving from the elapsed time data and user-supplied information length, stress and other parameters descriptive of the tensile load member, wherein the intelligent processing and control means include a general purpose digital computer, the computer providing control and timing signals to the time interval measuring means and the computer receiving elapsed time data from the time interval measuring means, and further wherein the computer comprises means for converting the elapsed time data into an elongation quantity and for converting the elongation quantity into a stress quantity; and means for supplying the user with the elongation and stress quantities.

2. The length and stress measuring apparatus, as recited in claim 1, wherein the general purpose digital computer also includes memory means for maintaining data tables of physical parameters corresponding to a plurality of tensile load member materials, operating temperatures and stress.

3. The length and stress measuring apparatus, as recited in claim 1, wherein the means for supplying the user with elongation and stress quantities include a visual display.

4. The length and stress measuring apparatus, as recited in claim 1, wherein the means for supplying the user with elongation and stress quantities include a printer.

5. The length and stress measuring apparatus, as recited in claim 1, wherein the means for supplying the user with elongation and stress quantities include a light-emitting diode readout.

6. The length and stress measuring apparatus, as recited in claim 1, wherein the means for supplying the user with elongation and stress quantities include a liquid crystal display readout.

7. An apparatus, for measuring the length and stress in a tensile load member, wherein a transducer is energized to insert an ultrasonic pulse into one end of the load member and the transducer receives an ultrasonic pulse echo which is reflected back to the transducer from the other end of the load member, the transducer converting the echo into an equivalent electrical signal, the apparatus comprising time interval measuring means for obtaining elapsed time data corresponding to the interval between the energizing of the transducer and the receipt of the pulse echo;

intelligent processing and control means which receive the elapsed time data and user supplied information for controlling the time interval measuring means and for deriving from the elapsed time data and user-supplied information length, stress and other parameters descriptive of the tensile load member, in which the intelligent processing means automatically convert the elapsed time data into an elongation quantity, wherein the intelligent processing means further compensate the elongation quantity for changes in the modulus of elasticity, the coefficient of expansion, and the sonic velocity for the tensile load member material due to changes in temperature.

8. An apparatus for measuring a time interval of the type in which an energizing signal is generated to indicate the start of the time interval, and a return signal is received to indicate the end of the time interval, the time interval measuring apparatus comprising a first reference signal having a predetermined phase and frequency, the first reference frequency being synchronized with the energizing signal;

a second reference signal having a predetermined phase and frequency, the frequency of the second reference signal being equal to that of the first reference signal and the second reference signal having a predetermined phase difference from the first reference signal;

counting means for counting the number of cycles of the first reference frequency which occur between the generation of the energizing signal and the receipt of the return signal; and error signal detecting means for deriving an error signal for modifying the cycle count to include the time interval falling between the last full cycle which is counted by the counting means and which occur prior to receipt of the return signal, and the receipt of the return signal, the error signal detecting means including means for measuring the interval between the receipt of the return signal and a subsequent specified state in the first reference signal;

means for measuring the interval between the receipt of the return signal and the occurrence of the subsequent specified state in the second reference signal; and means for selecting and identifying the longer of the first reference signal interval and the second reference signal interval; and means for converting the cycle count and selected reference signal interval into units of time.

9. The time interval measuring apparatus, as recited in claim 8, in which the return signal has a plurality of zero crossings and wherein the instant of receipt of the return signal is determined by and according to one of the first two zero-crossings which occur within the received return signal.

10. The time interval measuring apparatus, as recited in claim 8, further wherein the error signal detecting means accumulates a substantial number of error signals to derive a dynamic average error signal.

11. A method of measuring a time interval between the initiation of an energizing signal and the receipt of a return signal, comprising the steps of counting the number of cycles of a first clock which occur between the initiation of the energizing signal and the receipt of the return signal, the first clock being synchronized to the initiation of the energizing signal and having a predetermined frequency;

generating a second clock having the same frequency as the first clock and having a predetermined phase shift from the first clock;

measuring a first clock interval between the receipt of the return signal and a subsequent specified state in the first clock and a second clock interval between the receipt of the return signal and the occurrence of the subsequent specified state in the second clock;

selecting the longer of the first clock interval and the second clock interval;

compensating the selected clock interval for the phase difference between the first clock and the second clock;

combining the cycle count with the compensated selected clock interval; and converting the combined cycle count and compensated selected clock interval into units of time.

12. The method of measuring a time interval between the initiation of an energizing signal and the receipt of a return signal, as recited in claim 11, wherein in the clock interval measuring step, the subsequent specified state is the first occurrence of a rising edge in the clock waveform following receipt of the return signal.

13. The method of measuring a time interval between the initiation of an energizing signal and the receipt of a return signal, as recited in claim 11, wherein in the clock measuring step the subsequent specified state is the first occurrence of a falling edge in the clock waveform following receipt of the return signal.

14. A method of measuring the length and stress in a tensile load member of the type including the steps of energizing a transducer to insert an ultrasonic pulse into the load member and receiving a subsequent ultrasonic pulse echo from the load member, the method comprising the steps of measuring the time interval between the insertion of the ultrasonic pulse and the receipt of the pulse echo in the unloaded tensile load member;

measuring the time interval between the insertion of the ultrasonic pulse and the receipt of the pulse echo in the loaded tensile member;

converting the unloaded-member time interval into a reference length according to a velocity factor;

converting the loaded-member time interval into a loaded length, the conversion including the steps of adjusting the velocity factor used in the calculations for the change in velocity in stressed materials; and adjusting the velocity factor to apply to that length of the tensile load member which is under stress; and calculating stress by application of Hooke's law to the difference between the reference length and the loaded length.

15. The method of measuring the length and stress in a tensile load member, as recited in claim 14, further including the step of adjusting the reference length and the loaded length for change in length due to temperature effects according to a temperature factor.

16. An apparatus for measuring the length and stress in a tensile load member, wherein a transducer is energized to insert an ultrasonic pulse into one end of the load member and the transducer receives an ultrasonic pulse echo which is reflected back to the transducer from the other end of the load member, the transducer converting the echo into an equivalent electrical signal, the apparatus comprising time interval measuring means for obtaining elapsed time data corresponding to the interval between the transducer energization and the receipt of the pulse echo, wherein the time interval measuring means generate a first and a second clock, the first clock having the same frequency as the second clock, the second clock having a predetermined phase difference from the first clock, the time interval measuring means further including means for counting the number of cycles of the second clock which occur during the interval, and error detecting means for detecting the time interval between the receipt of the pulse echo and the occurrence of a specified state in the first clock and in the second clock; and intelligent processing and control means which receive the elapsed time data and user supplied information for controlling the time interval measuring means and for deriving from the elapsed time data and user-supplied information, length, stress and other parameters descriptive of the tensile load member.

* * * * *